United States Patent
Ha et al.

(10) Patent No.: US 10,459,093 B2
(45) Date of Patent: Oct. 29, 2019

(54) PET-MRI DEVICE AND MANUFACTURING METHOD THEREOF

(71) Applicant: KOREA ATOMIC ENERGY RESEARCH INSTITUTE, Daejeon (KR)

(72) Inventors: Jang Ho Ha, Jeollabuk-do (KR); Han Soo Kim, Jeollabuk-do (KR); Young Soo Kim, Daejeon (KR); Manhee Jeong, Incheon (KR); Sun Mog Yeo, Daejeon (KR)

(73) Assignee: KOREA ATOMIC ENERGY RESEARCH INSTITUTE, Daejeon (KR)

( * ) Notice: Subject to any disclaimer, the term of this patent is extended or adjusted under 35 U.S.C. 154(b) by 492 days.

(21) Appl. No.: 15/153,138

(22) Filed: May 12, 2016

(65) Prior Publication Data
US 2016/0252633 A1 Sep. 1, 2016

Related U.S. Application Data

(63) Continuation of application No. PCT/KR2014/002602, filed on Mar. 27, 2014.

(30) Foreign Application Priority Data

Dec. 30, 2013 (KR) .................. 10-2013-0166828

(51) Int. Cl.
*G01T 1/29* (2006.01)
*A61B 5/055* (2006.01)
(Continued)

(52) U.S. Cl.
CPC .......... *G01T 1/2985* (2013.01); *A61B 5/0035* (2013.01); *A61B 5/055* (2013.01);
(Continued)

(58) Field of Classification Search
CPC ..... G01T 1/2985; G01T 1/241; A61B 5/0035; A61B 5/055; A61B 5/037; G01R 33/28; G01R 33/381
See application file for complete search history.

(56) References Cited

U.S. PATENT DOCUMENTS

| | | | |
|---|---|---|---|
| 2002/0105328 A1* | 8/2002 | Goto | G01R 33/3875 324/307 |
| 2007/0055127 A1* | 3/2007 | Ladebeck | G01R 33/481 600/407 |

(Continued)

FOREIGN PATENT DOCUMENTS

| | | |
|---|---|---|
| JP | 5322277 B2 | 10/2013 |
| KR | 2008-0105443 A | 12/2008 |

(Continued)

OTHER PUBLICATIONS

J. Adams ; B. W. Manley; The Mechanism of Channel Electron Multiplication; Date of Publication: Jun. 1966; Published in: IEEE Transactions on Nuclear Science (vol. 13, Issue: 3); pp. 88-99.*

(Continued)

*Primary Examiner* — Amanda Lauritzen Moher
*Assistant Examiner* — Chao Sheng
(74) *Attorney, Agent, or Firm* — Lando & Anastasi, LLP

(57) ABSTRACT

A PET-MRI device and a manufacturing method thereof are disclosed. The PET device includes a magnetic resonance imaging (MRI) machine comprising a solenoid coil and a magnetic-field correction coil, wherein the MRI machine has a cylindrical structure or a dipole structure; and a positron emission tomography (PET) machine comprising a PET image sensor, wherein PET image sensor electrodes are formed on one and the other ends of the PET image sensor that have a doughnut shape, and the PET machine has a cylindrical structure or a lattice structure, wherein the PET machine is formed in the MRI machine to allow a direction (Continued)

of an electric field of the PET machine to be parallel to a direction of a magnetic field of the MRI machine.

7 Claims, 4 Drawing Sheets

(51) Int. Cl.
    *A61B 6/03*     (2006.01)
    *A61B 5/00*     (2006.01)
    *G01R 33/28*     (2006.01)
    *G01R 33/381*     (2006.01)
    *G01T 1/24*     (2006.01)

(52) U.S. Cl.
    CPC .............. *A61B 6/037* (2013.01); *G01R 33/28* (2013.01); *G01R 33/381* (2013.01); *G01T 1/241* (2013.01)

(56) References Cited

U.S. PATENT DOCUMENTS

| | | | |
|---|---|---|---|
| 2008/0042069 A1* | 2/2008 | Drezet | G01T 1/2985 250/370.09 |
| 2008/0214927 A1 | 9/2008 | Cherry et al. | |
| 2010/0102813 A1* | 4/2010 | Schulz | A61B 6/037 324/309 |
| 2010/0217112 A1 | 8/2010 | Choi et al. | |
| 2011/0288401 A1* | 11/2011 | Solf | A61B 6/037 600/411 |
| 2015/0234058 A1* | 8/2015 | Engel | G01T 1/241 250/370.08 |

FOREIGN PATENT DOCUMENTS

| | | |
|---|---|---|
| KR | 101047662 B1 | 7/2011 |
| KR | 2012-0057601 A | 6/2012 |
| KR | 2013-0013293 A | 2/2013 |

OTHER PUBLICATIONS

Richard P. Feynman; Robert B. Leighton; Matthew Sands; The Feynman Lectures on Physics vol. 2, 2nd edition; Date of Publication: Jan. 8, 2011; publisher Addison Wesley; Chapter 29.*

* cited by examiner

E →
B -------→
E x B = 0

PET-MRI DEVICE AND MANUFACTURING METHOD THEREOF

CROSS-REFERENCE TO RELATED APPLICATIONS

This application is a continuation application of International (PCT) Patent Application Serial No. PCT/KR2014/002602 filed on Mar. 27, 2014 which, in turn, claims the benefit of priority to Korean Patent Application Serial No. KR 10-2013-0166828 filed on Dec. 30, 2013, the entire disclosure of each of which is hereby incorporated herein by reference in its entirety for all purposes.

TECHNICAL FIELD

The present disclosure relates to a PET-MRI device and manufacturing method thereof, and more particularly, to a PET device being not affected by a magnetic field and manufacturing method thereof.

BACKGROUND ART

Medical images used for diagnosis of cells, pre-clinical study, clinical study, and patients are generally classified into structural images and functional images. The structural images mean the structural and anatomical images of human bodies and the functional images are obtained by imaging functional information on the metabolic functions of the human bodies by using a direct or indirect method. A structural and anatomical imaging technology includes computed tomography (CT) and magnetic resonance imaging (MRI), and positron emission tomography (PET) is being widely used as a technology that images functional information by observing the physiological and biochemical actions of the human bodies.

PET is a powerful biological imaging tool that meters the functions of the human bodies by using a non-invasive method. PET injects, into the human bodies, biological probe molecules labeled as positron emission isotope having radioactive activation, realigns and images the distribution of radioactivity by using tomography to be able to quantify the physiological and physiochemical reactions in each of organs in the human bodies. Functional/molecular information on the structures of the human bodies such as brain and organs provided by PET may be usefully used for finding the cause of a disease, determining a prognosis and observing progress after anticancer treatments.

Also, PET provides functional information on the tissues in the human body with molecule-level sensitivity and its concept is developing to hybrid PET medical imaging equipment such as a PET-CT hybrid device or a PET-MRI imaging device.

FIG. 1 is a diagram for explaining the structure of a typical, cylindrical MRI.

Referring to FIG. 1, a typical MRI machine 100 includes a solenoid coil 150 that uniformly generates a magnetic field, and a magnetic-field correction coil. The direction B, 120 of a magnetic field of the MRI machine 100 is formed in the length direction of a cylinder.

The MRI machine 100 generates a high frequency electromagnetic wave while a human body is in a large cylinder generating the magnetic field, allows hydrogen atoms around the human body to resonate, measures the difference between signals emitting from each tissue, realigns and images the hydrogen atoms through a computer. That is, the MRI machine 100 emits a high frequency electromagnetic wave from its magnet device to a human body, receives it back if a signal such as echo is emitted, converts the signal into position related digital information and makes the digital information as images.

FIG. 2 is a diagram for explaining the structure of a typical, cylindrical conventional PET machine.

Referring to FIG. 2, the typical PET machine 200 has a doughnut-shaped cylindrical structure and includes a PET image sensor electrode 250. The PET image sensor electrodes 250 are formed on the external and internal circumferential regions of a cylinder. Thus, the direction E, 220 of an electric field of the PET machine 200 is formed perpendicularly to the length direction of the cylinder.

After a positron emitted from radioactive isotope is emitted, it exhausts its own kinetic energy for a very short time, combines with a neighboring electron in atom and is annihilated, in which case two annihilation radiations are emitted at an angle of 180□. The PET machine 200 is a module for detecting the two annihilation radiations that are emitted together.

The PET-MRI device has both the function of the PET machine 200 representing 3D physiochemical, functional images of human bodies by using radioactive medicine and medical supplies emitting positrons and the function of the MRI machine 100 performing 3D examination on the tissues and blood vessels of human bodies by using a superconductive magnet and a radio high frequency radio-wave. That is, the PET-MRI device is a hybrid molecular imaging system in which the PET machine 200 showing supersensitive molecular images is combined with the MRI machine 100 showing high-resolution functional images. Accordingly, the PET-MRI device provides enhancement of diagnosis accuracy, a new image bio-marker, new medicine development, a decrease in radiation exposure and enhancement of patient convenience.

Currently, the PET-MRI device includes the PET machine 200 in the MRI machine 100 and uses several methods so that the image sensor of the PET machine is less affected by a magnetic field in an integration process. Among others, it uses a radioactivity reacting material of a scintillator, a photomultiplier tube converting a visible light generated from the material into an electron, or a thin silicon based semiconductor light-receiving sensor.

However, the MRI machine fundamentally fails to remove an effect on a magnetic field in all cases. Thus, it is true that the efficiency of the PET-MRI device decreases.

Korean patent publication No. 2012-0057601 relates to a method of removing noise from PET signal in a PET-MRI hybrid device using filtering and PET machine in a PET-MRI hybrid device using the same.

DISCLOSURE OF THE INVENTION

Technical Problem

One object of the present invention is to provide a PET-MRI device in which a PET image sensor is not affected by a magnetic field fundamentally, and a manufacturing method thereof.

Another object of the present invention is to provide a PET-MRI device which uses a high-performance radioactive image advanced material that has not been utilized due to an effect of a magnetic field, and a manufacturing method thereof.

Technical Solution

In order to achieve the objects, the present invention provides a PET-MRI device including: a magnetic resonance imaging (MRI) machine comprising a solenoid coil and a magnetic-field correction coil, wherein the MRI machine has a cylindrical structure; and a positron emission tomography (PET) machine comprising a PET image sensor, wherein PET image sensor electrodes are formed on one and the other ends of the PET image sensor that have a doughnut shape, and the PET machine has a cylindrical structure, wherein the PET machine is formed in the MRI machine to allow a direction of an electric field of the PET machine to be parallel to a direction of a magnetic field of the MRI machine.

The present invention also provides a PET-MRI device including: an MRI machine having a dipole structure in which an upper magnet and a lower magnet are spaced apart from each other; and a PET machine having a lattice structure comprising a first and a second PET image sensor, the first and the second PET image sensors having a horizontal bar shape, wherein the first and the second PET image sensors are spaced apart in parallel to each other, and the first and the second PET image sensors are formed between the upper magnet and the lower magnet to allow a direction of an electric field of the PET machine to be parallel to a direction of a magnetic field of the MRI machine.

The present invention also provides a method of manufacturing a PET-MRI device including: providing an MRI machine; providing a PET machine;

including the PET machine in the MRI machine to allow the direction of the magnetic field of the MRI machine to be parallel to the direction of the electric field of the PET machine.

Advantageous Effects

According to the PET-MRI device and the manufacturing method thereof according to the present invention, the PET image sensor may not be affected by the magnetic field fundamentally.

Also, it is possible to use a high-performance radioactive image advanced material that has not been utilized due to the magnetic field.

Also, since the PET image sensor has a structure that is not affected by the magnetic field, there may be no need for separately developing a material that is not affected by the magnetic field.

MODE FOR CARRYING OUT THE INVENTION

Figure 1:
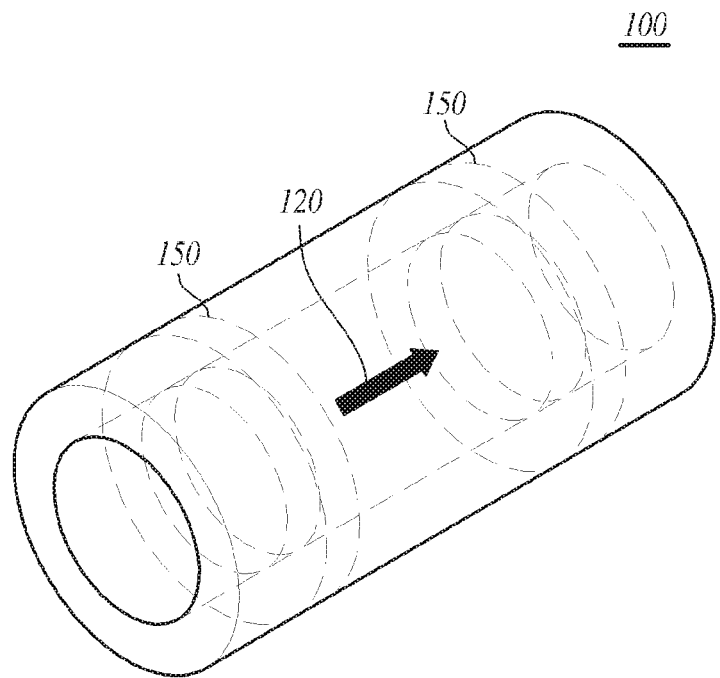
FIG. 1 is a diagram for explaining the structure of a typical MRI machine.
Figure 2:
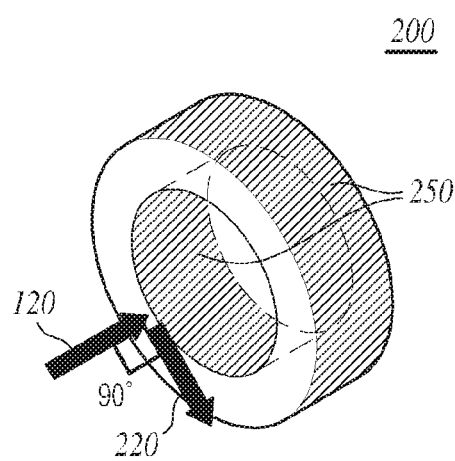
FIG. 2 is a diagram for explaining the structure of a typical PET machine.

Embodiments of the present invention are described below in detail with reference to the accompanying drawings. It should be noted that when adding reference numerals to components of each drawing, the same components have the same numeral wherever possible even though they are shown in different drawings. Also, in describing the present invention, detailed descriptions of related known configurations or functions are not provided if it is determined that they obscure the subject matter of the present invention.

Figure 3:
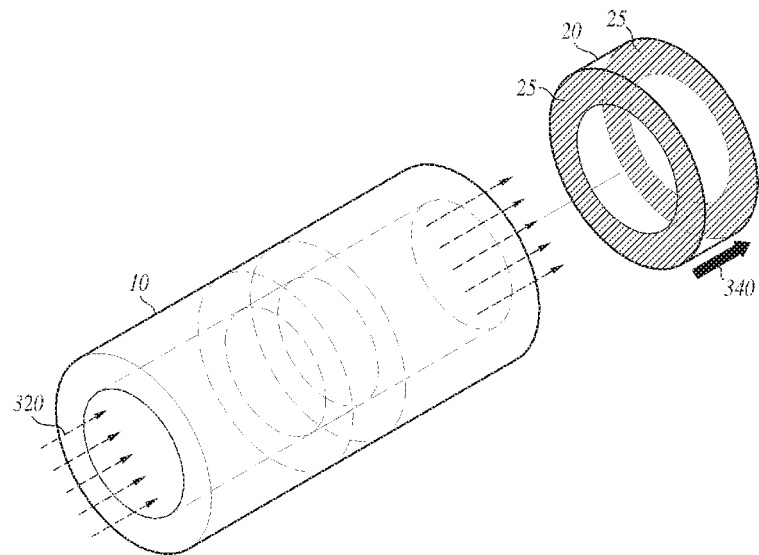
FIG. 3 is a diagram for explaining the structures of cylindrical PET and MRI machines according to an embodiment of the present invention.

FIG. 3 is a diagram for explaining the structures of cylindrical PET and MRI machines according to an embodiment of the present invention.

Referring to FIG. 3, the MRI machine 10 and the PET machine 20 may perform tomography on a user. The MRI machine may perform tomography on a user by using magnetic resonance. The PET machine 20 may perform tomography on a user by using positron emission.

The MRI machine 10 may include a solenoid coil and a magnetic-field correction coil. The MRI machine 10 may have a cylindrical structure and may have a hollow doughnut shape. The MRI machine 10 may include a solenoid coil to uniformly generate a magnetic field. The solenoid coil may be in plurality, in which case a plurality of solenoid coils may be at regular intervals. Accordingly, the MRI machine 10 may generate a magnetic field. Also, the direction 320 of the magnetic field may be the same as the length direction of the MRI machine 10.

The PET machine 20 may include a PET image sensor electrode 25. The PET machine 20 may have a cylindrical structure and may have a hollow doughnut shape. The PET image sensor electrodes 25 may be formed on one and the other ends of the doughnut shaped PET machine 20. Accordingly, the PET machine 20 may generate an electric field. The direction 340 of the electric field is the same as the length direction of the PET machine 20.

The PET machine 20 may be formed through the insertion into a certain region of the MRI machine 10. The inserted PET machine 20 may be combined with the MRI machine 10 to become the PET-MRI device. Also, the region where the magnetic field is uniformly generated may be a part of the MRI machine 10 that is indicated by broken lines.

Figure 4:
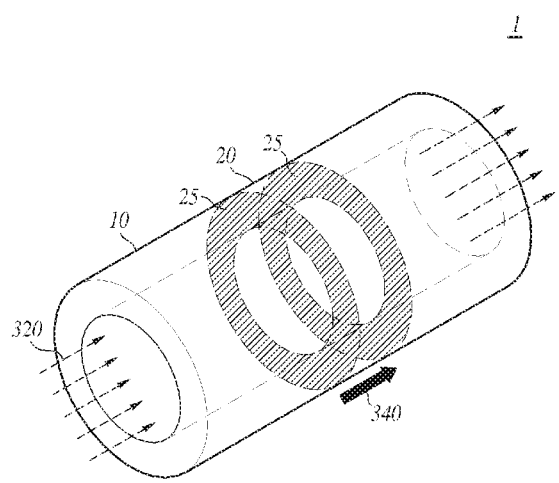
FIG. 4 is a diagram for explaining the structure of a cylindrical PET-MRI device according to an embodiment of the present invention.

FIG. 4 is a diagram for explaining the structure of a cylindrical PET-MRI device according to an embodiment of the present invention.

Referring to FIG. 4, a PET-MRI device 1 may have a cylindrical, hollow shape. The PET-MRI device 1 may have a doughnut-shaped cross-sectional view when cutting the device in a circumferential direction. Also, the PET-MRI device 1 may be obtained by combining the cylindrical PET machine 20 with the cylindrical MRI machine 10.

The PET-MRI device 1 may be formed by inserting the cylindrical PET machine 20 into the cylindrical MRI machine 10. The PET-MRI device 1 may be formed by inserting the PET machine 20 into a region of the MRI machine 10 where a magnetic field is uniform.

The MRI machine 10 may be cylindrical and may have a hollow doughnut shape. The MRI machine 10 may include a solenoid coil and a magnetic-field correction coil. The MRI machine 10 may include the solenoid coil and the magnetic-field correction coil at a certain distance. Also, the MRI machine 10 may include a plurality of solenoid coils.

The solenoid coil is formed by uniformly winding a coil around a long cylinder several times, and when currents flow through the coil, a magnetic field outside the cylinder is nearly zero but the inside of the cylinder forms a magnetic field having a relatively uniform magnitude. In this case, the magnitude of an inside magnetic field is proportional to the magnitude of currents and to the number of windings of a coil per unit length.

The magnetic-field correction coil corrects a tiny region of a magnetic field generated from the solenoid coil so that a uniform magnetic field is generated.

Thus, the MRI machine 10 may generate a uniform magnetic field. The direction B, 320 of the magnetic field may be the same as the length direction of the MRI machine 10.

The PET machine 20 may be cylindrical and may have a hollow doughnut shape. The PET machine 20 may include PET image sensor electrodes 25 formed on one and the other ends of the doughnut shaped PET machine 20. The PET image sensor electrode 25 may generate an electric field inside sensing material. The PET image sensor may include a combination of a scintillator and a silicon semiconductor or a single compound semiconductor.

The direction E, 340 of the electric field may be from one end of the doughnut-shaped PET machine to the other end. That is, the direction 340 of the electric field is the same as the length direction of the PET machine 20.

The PET-MRI device 1 is designed so that the direction 340 of the electric field of the PET machine 20 is substantially parallel to the direction 320 of the magnetic field of the MRI 10. To this end, the PET-MRI device 1 of the present invention forms both ends of the PET machine 20 on a certain region of the MRI machine 10 to be parallel to the circumferential direction of both ends of the MRI machine 10. Then, the PET image sensor electrodes 25 are formed on both ends of the PET machine 20.

Also, the PET-MRI device 1 may form the PET machine on a region where a magnetic field is uniform. In particular, the PET-MRI device 1 may arrange the PET machine 20 in the middle of the MRI machine 10.

The PET-MRI device may fundamentally block the PET machine 20 from a magnetic field because the direction 320 of the magnetic field is parallel to the direction 340 of the electric field due to such a arrangement.

For the PET-MRI device 1, a charge particle moving in the magnetic field may be provided a force by Equation 1. That is, Equation 1 represents the relationship between the provided force and the charge particle moving the magnetic field.

$$\vec{F} = q\vec{v} \times \vec{B}$$ <Equation 1>

In this example, $\vec{F}$ means the direction of a force, q means a charge, $\vec{v}$ means the velocity of a charge particle, and $\vec{B}$ means the magnetic field strength of an MRI machine. In particular, $\vec{v}$ may be velocity of charge particles (electron or holes) generated by applied voltage to the PET image sensor electrode 25 reacting to radioactivity.

If the PET image sensor electrodes 25 are formed on one and the other ends of the doughnut shaped PET machine like the PET-MRI device 1, Equation 2 may be calculated based on Equation 1. Equation 2 represents that the movement direction of the charge particle is proportional to the direction of an electric field.

$$\vec{v} \propto \vec{E}$$ <Equation 2>

In this example, $\vec{E}$ means the direction of an electric field inside a PET image sensor.

A force affecting electrons or a holes generated in a semiconductor inside a magnetic field may yield Equation 3 based on Equations 1 and 2. Equation 3 represents that a provided force, a charge particle moving in a magnetic field and an electric field in the magnetic field are proportional to one another.

$$\vec{F} \propto \vec{v} \times \vec{B} \propto \vec{E} \times \vec{B}$$ <Equation 3>

The PET-MRI device 1 may apply Equation 3. Also, the PET-MRI device 1 may apply Equation 4 because an electric field in PET has a direction parallel to a magnetic field in MRI. The electric field and the magnetic filed may have the same or opposite direction.

$$\vec{E} \times \vec{B} = 0$$ <Equation 4>

Equation 4 represents that the direction of an electric field in a magnetic field is parallel to the direction of the magnetic field and thus the electric field and the magnetic field provide a force of zero to each other.

That is, for the PET-MRI device 1, the electric field and the magnetic field may provide a force of zero to each other. For the PET-MRI device 1, a magnetic field generated at the MRI machine 10 may not fundamentally affect an electric field generated at the PET machine 20. Also, when a PET image sensor in a magnetic field generates an electron or a hole by radioactivity, the electron or holes generating in PET-MRI device 1 moves circularly before the electron reaches an electrode by an electric field. Accordingly, the PET-MRI device 1 may hit nearby atoms through the circular movement, generate a secondary electron and further induce the amplification of a charge.

Accordingly, the PET-MRI device 1 may utilize a radioactive image advanced material which has excellent efficiency and characteristics.

Figure 5:
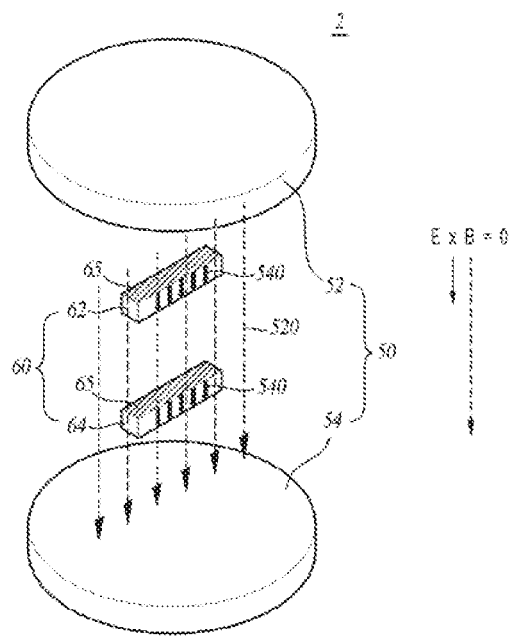
FIG. 5 is a diagram for explaining the structure of an open PET-MRI device according to an embodiment of the present invention.

FIG. 5 is a diagram for explaining the structure of an open PET-MRI device according to an embodiment of the present invention.

Referring to FIG. 5, the PET-MRI device 2 may have an open shape. The PET-MRI device 2 may include a dipole type MRI machine 50 and a lattice type PET machine 60.

The MRI machine 50 may include an upper magnet 52 and a lower magnet 54. The upper magnet 52 and the lower magnet 54 may be dipole magnets. The dipole magnet may also use a permanent magnet to generate a magnet field. The upper magnet 52 and the lower magnet 54 may be spaced apart in parallel to each other. The upper magnet 52 may be arranged over the lower magnet 54. Also, the upper magnet 52 and the lower magnet 54 may be similar to each other and be arranged to face each other.

The bottom of the upper magnet 52 may be an N pole or an S pole. The upper magnet 52 may be one of a circular plate, a triangular plate, a quadrilateral plate and a polygonal plate. The top of the lower magnet 54 may be an S pole or an N pole to match the upper magnet 52. The lower magnet 54 may be one of a circular plate, a triangular plate, a quadrilateral plate and a polygonal plate.

For the MRI machine 50, a magnetic field may be formed from the upper magnet 52 to the lower magnet 54 and from the lower magnet 54 to the upper magnet 52. That is, the direction 520 of the magnetic field may be one of a downward direction and an upward direction.

The PET machine 60 may include two PET image sensors, a first PET image sensor 62 and a second PET image sensor 64 that have a horizontal bar shape. The first PET image sensor 62 may be arranged over the second PET image sensor 64. The first PET image sensor 62 may be arranged in parallel to the second PET image sensor 64. Also, the first PET image sensor 62 may be similar to the second PET image sensor 64 and be arranged to face each other.

The first PET image sensor 62 may be formed by a plurality of PET image sensors each of which includes double electrodes on the top and the bottom. The top of the electrode 65 of the PET image sensor may be a (+) pole and the bottom thereof may be a (−) pole. Alternatively, the top of the electrode 65 of the PET image sensor may be a (−) pole and the bottom thereof may be a (+) pole. The first PET image sensor 62 may form a horizontal bar shape because the plurality of PET image sensors are connected in a horizontal direction.

The second PET image sensor 64 may be formed by a plurality of PET image sensors each of which includes dual electrodes on the top and the bottom. The top and bottom of the electrode 65 of the PET image sensor may be formed as the same polarities as those of the electrode of the first PET image sensor 62. The second PET image sensor 64 may form a horizontal bar shape because the plurality of PET image sensors are connected in a horizontal direction.

For the PET machine 60, an electric field may be formed from the first PET image sensor 62 toward the second PET image sensor 64. That is, the direction E 540 of the electric field may be a downward direction. Alternatively, the direction 540 of the electric field may be an upward direction.

Thus, for the PET-MRI device 2, the direction 540 of the electric field may be parallel to the direction 520 of the magnetic field. The direction 540 of the electric field and the direction 520 of the magnetic filed may be the same or opposite direction. The PET-MRI device 2 may apply Equation 4. That is, for the PET-MRI device 2, the electric field and the magnetic field may provide a force of zero to each other.

The PET-MRI device 2 may have a downward geometry so that the direction 540 of the electric field is parallel to the direction 520 of the magnetic field. For the PET-MRI device 20, the upper magnet 52, the first PET image sensor 62, the second PET image sensor 64 and the lower magnet 54 may be arranged sequentially in a downward direction. Also, the components of The PET-MRI device 2 may be spaced apart at a certain distance.

Thus, for the PET-MRI device 2, a magnetic field generated at the MRI machine 50 may not fundamentally affect an electric field generated at the PET machine 60. Also, when a PET image sensor in the magnetic field generates an electron or a hole by radioactivity, the PET-MRI device 2 circularly moves an electron before the electron reaches an electrode by an electric field. Accordingly, the PET-MRI device 2 may hit nearby atoms through the circular movement, generate a secondary electron and further induce the amplification of a charge.

Accordingly, the PET-MRI device 2 may utilize a radioactive image advanced material which has excellent efficiency and characteristics.

Figure 6:
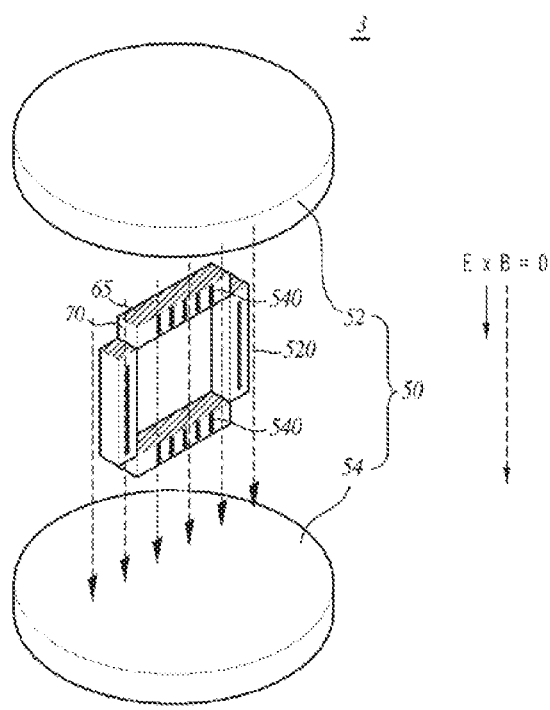
FIG. 6 is a diagram for explaining the structure of an open PET-MRI device according to another embodiment of the present invention.
Figure 7:
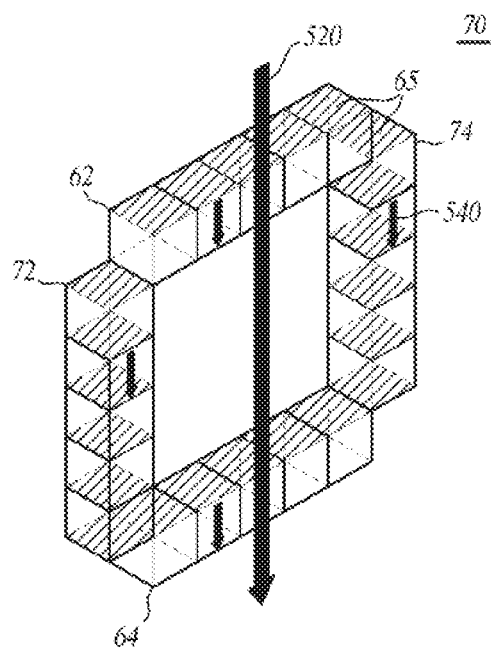
FIG. 7 is a diagram for explaining the structure of a PET machine of FIG. 6 in more detail.

FIG. 6 is a diagram for explaining the structure of an open PET-MRI device according to another embodiment of the present invention, and FIG. 7 is a diagram for explaining the structure of a PET machine of FIG. 6 in more detail.

Referring to FIGS. 6 and 7, a PET-MRI device 3 may be another embodiment of the PET-MRI device 3. The PET machine 3 may further include a third PET image sensor 72 and a fourth PET image sensor 74 compared to the PET-MRI device. Accordingly, the PET-MRI device 3 may generate a stronger electric field.

A PET-MRI device 3 may include the MRI machine 50 including the upper magnet 52 and the lower magnet 54, and a PET machine 70 including the first PET image sensor 62, the second PET image sensor 64, a third PET image sensor 72, and a fourth PET image sensor.

The PET machine 70 may include the first PET image sensor 62 and the second PET image sensor 64 that have a horizontal bar shape, and the third PET image sensor 72 and the fourth PET image sensor 74 that have a vertical bar shape. The first PET image sensor 62 and the second PET image sensor 64 may be parallel to each other, and the third PET image sensor 72 and the fourth PET image sensor 74 may also be parallel to each other.

The PET machine 70 may form a ring shape because the first PET image sensor 62, the second PET image sensor 64, the third PET image sensor 72 and the fourth PET image sensor 74 are connected to one another. That is, the first PET image sensor 62 may be connected to the third PET image sensor 72 and the fourth PET image sensor 74, the second PET image sensor 64 may be connected to the third PET image sensor 72 and the fourth PET image sensor 74. The third PET image sensor 72 may be connected to the first PET image sensor 62 and the second PET image sensor 64, and the fourth PET image sensor 74 may be connected to the first PET image sensor 62 and the second PET image sensor 64.

The PET image sensor electrodes 65 may be formed with different polarities on the top and bottom of the third PET image sensor 72. The third PET image sensor 72 may form a vertical bar shape because a plurality of PET image sensors are stacked. The third PET image sensor 72 may be formed by stacking the plurality of PET image sensors in which a (+) pole and a (−) pole are respectively formed as a unit sensor.

The PET image sensor electrodes 65 may be formed with different polarities on the top and bottom of the fourth PET image sensor 74. The fourth PET image sensor 74 may form a vertical bar shape because a plurality of PET image sensors are stacked. The fourth PET image sensor 74 may be formed by stacking the plurality of PET image sensors in which a (+) pole and a (−) pole are respectively formed as a unit sensor.

The top and bottom of each of the third and fourth PET image sensor electrodes 65 are formed to have the same polarities as those of each of the first and second PET image sensor electrodes 65.

The directions 540 of electric fields of the third PET image sensor 72 and the fourth PET image sensor 74 may be downward because the PET image sensor electrode 65 is formed to have a (+) pole and a (−) pole per unit sensor. Alternatively, the direction 54 of the electric field may be an upward direction.

Thus, the directions of electric fields of the third PET image sensor 72 and the fourth PET image sensor 74 may be the same as those of electric fields of the first PET image sensor 62 and the second PET image sensor 64. In particular, since the direction 520 of an electric field needs to form a direction in a stacked structure of the first to the fourth PET image sensors 62, 64, 72 and 74, it may be selected as an upward direction or a downward direction.

For the PET-MRI device 3, the direction 540 of the electric field may be parallel to the direction 520 of the magnetic field. The direction 540 of the electric field and the direction 520 of the magnetic filed may be the same or opposite direction. The PET-MRI device 3 may apply Equation 4. That is, for the PET-MRI device 3, the electric field and the magnetic field may provide a force of zero to each other.

The PET-MRI device 3 may have a downward geometry so that the direction 540 of the electric field is parallel to the direction 520 of the magnetic field. For the PET-MRI device 3, the upper magnet 52, the ring-shaped PET machine 70, and the lower magnet 54 may be arranged sequentially in a downward direction.

Thus, for the PET-MRI device 3, a magnetic field generated at the MRI machine 50 may not fundamentally affect an electric field generated at the PET machine 70. Also, when a PET image sensor in the magnetic field generates an electron or a hole by radioactivity, the PET-MRI device 3 circularly moves an electron before the electron reaches an electrode by an electric field. Accordingly, the PET-MRI device 3 may hit nearby atoms through the circular movement, generate a secondary electron and further induce the amplification of a charge.

Accordingly, the PET-MRI device 3 may utilize a radioactive image advanced material which has excellent efficiency and characteristics.

Figure 8:
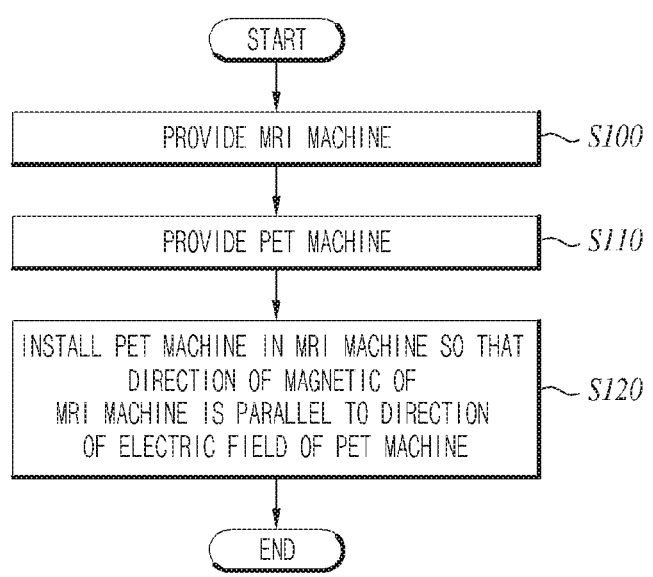
FIG. 8 is a flowchart of a method of manufacturing a PET-MRI device according to an embodiment of the present invention.

FIG. 8 is a flowchart of a method of manufacturing a PET-MRI device according to an embodiment of the present invention.

Referring to FIG. 8, the PET-MRI device may arrange the PET machine in a region of the MRI machine where a magnetic field and an electric field are generated so that they are parallel to each other. Thus, the electric field generated at the PET machine may not be affected by the magnetic field generated at the MRI machine. The PET-MRI device may be implemented by three steps.

The MRI machine is provided in step S100. The MRI machine may include a cylindrical structure and a dipole structure. The MRI machine may be one of a cylindrical type and an open type. The MRI machine may generate a uniform magnetic field.

When the MRI machine is of a cylindrical type, the direction of the magnetic field of the MRI machine may be a length direction. When the MRI machine is in a dipole structure, the direction of the magnetic field of the MRI machine may be one of a downward direction and an upward direction.

The PET machine is provided in step S110. The PET machine may include a cylindrical structure and a lattice structure. The PET machine may be provided to match the type of the MRI machine. The PET machine may generate a uniform electric field.

When the PET is in a cylindrical structure, the PET image sensor electrodes may be formed on one and the other ends of the doughnut shaped PET machine. Thus, the direction of the electric field of the cylindrical PET may be a length direction.

When the PET is in a lattice structure, the PET image sensor electrodes may be formed on the top and bottom of the PET machine. When a plurality of PET image sensors including the PET image sensor electrode are connected horizontally, the first and the second image sensor electrodes may be formed, and when the plurality of PET image sensors are stacked vertically, the third and the fourth image sensor electrodes may be formed. Thus, the direction of the electric field of the lattice type PET may be one of a downward direction and an upward direction.

The PET image sensor may include a combination of a scintillator and a silicon semiconductor or a single compound semiconductor.

The PET machine is included in the MRI machine so that the direction of the magnetic field of the MRI machine and that of the electric field of the PET machine are parallel to each other in step S120. The PET machine may be included in a region of the MRI machine where the magnetic field is uniform. Also, the PET machine may be formed in the MRTI machine so that the direction of the electric field is parallel to the direction of the magnetic field.

That is, the direction of the electric field may be any one of the same or opposite direction to that of the magnetic field.

Although exemplary embodiments have been illustrated and described above, the present disclosure is not limited specific embodiments described above but may be varied by a person skilled in the art without departing from the subject matter of the present disclosure claimed in the following claims. Further, these variations are within the scope of the claims.

The invention claimed is:

1. A PET-MRI device, comprising:
a magnetic resonance imaging (MRI) machine comprising a solenoid coil and a magnetic-field correction coil, wherein the MRI machine has a cylindrical structure; and
a positron emission tomography (PET) machine comprising a PET image sensor, wherein unitary doughnut shaped PET image sensor electrodes are formed on ends of the PET image sensor which consists essentially of a single compound semiconductor, and the PET machine has a cylindrical structure,
wherein the PET machine is formed in the MRI machine and is configured to have a direction of an electric field of the PET machine that is parallel to a direction of a static magnetic field (B0) of the MRI machine by arranging the PET image sensor electrodes parallel to each other and a normal line of an electrode surface of each PET image sensor electrode parallel to the direction of the static magnetic field (B0).

2. The PET-MRI device of claim 1, wherein the direction of the static magnetic field (B0) is a length direction of the MRI machine, and the direction of the electric field of the PET machine is any one of the same direction or an opposite direction to the direction of the static magnetic field (B0).

3. The PET-MRI device of claim 1, wherein the PET machine is formed in a region of the MRI machine in which the static magnetic field (B0) is uniform.

4. The PET-MRI device of claim 1, wherein the static magnetic field (B0) of the MRI machine and the electric field of the PET machine that are parallel to each other are not affected by each other according to the following equation:

$$\vec{E} \times \vec{B} = 0$$

where $\vec{E}$ is the direction of the electric field in the PET machine and $\vec{B}$ is the direction of the static magnetic field (B0) in the MRI machine.

5. The PET-MRI device of claim 1, wherein when an electron or a hole is generated by radioactivity, the PET image sensor circularly moves the electron before the electron reaches one of the PET image sensor electrodes by the electric field of the PET machine, hits nearby atoms through a circular movement, generates a secondary electron and further induces amplification of a charge.

6. A method of manufacturing a PET-MRI device, the method comprising:

providing an MRI machine;

providing a cylindrical PET machine comprising a PET image sensor, wherein unitary doughnut shaped PET image sensor electrodes are formed on one and the other ends of the PET image sensor which consists essentially of a single compound semiconductor; and including the PET machine in the MRI machine to allow a direction of a static magnetic field (B0) of the MRI machine to be parallel to a direction of the electric field of the PET machine by arranging the PET image sensor electrodes parallel to each other and a normal line of the electrode surface of each PET image sensor electrode parallel to the direction of the static magnetic field (B0).

7. The method of claim 6, wherein the including of the PET machine in the MRI machine comprises including the PET machine in a region of the MRI machine in which the static magnetic field (B0) is uniform.

\* \* \* \* \*